United States Patent [19]
Scotchie

[11] Patent Number: 6,008,413
[45] Date of Patent: Dec. 28, 1999

[54] PROCESS FOR RECRYSTALLIZING 1,3-BIS (AMINOPHENOXY BENZENE)

[75] Inventor: Lawrence J. Scotchie, Charlotte, N.C.

[73] Assignee: National Starch and Chemical Investment Holding Corporation, Wilmington, Del.

[21] Appl. No.: 09/231,039

[22] Filed: Jan. 14, 1999

[51] Int. Cl.[6] .................. C07C 209/00; C07C 213/00
[52] U.S. Cl. ............ 564/438; 564/430; 564/437
[58] Field of Search .................. 564/438, 430, 564/437

[56] References Cited

U.S. PATENT DOCUMENTS 4,692,554 9/1987 Yamaguchi et al. .................. 564/430

FOREIGN PATENT DOCUMENTS 154746 5/1992 Japan .
9095533 4/1997 Japan .

OTHER PUBLICATIONS

St. Clair, A. et al. Polym. Mater. Sci Eng. (1984) 51 62–6.

*Primary Examiner*—Paul J. Killos
*Attorney, Agent, or Firm*—Jane E. Gennaro

[57] ABSTRACT

A process for purifying 1,3-bis(aminophenoxy benzene) (APB) on a manufacturing scale to at least 99.5% purity comprises the sequential steps of (a) forming the dihydrochloride salt of APB (hereinafter APB-HCl), (b) recrystallizing the APB-HCl from isopropyl alcohol, and (c) converting the APB-HCl to free APB.

1 Claim, No Drawings

PROCESS FOR RECRYSTALLIZING 1,3-BIS (AMINOPHENOXY BENZENE)

FIELD OF THE INVENTION

This invention is a process for recrystallizing 1,3-bis (aminophenoxy benzene) to obtain a purity of 99.5% or greater.

BACKGROUND OF THE INVENTION

The monomer 1,3-bis(aminophenoxy benzene), or APB, is a key monomer used to make heat-resistant high molecular weight polymers, particularly polyamides and polyimides. Preparation processes for APB results in product that approaches 99% purity; however, even at this level of purity, the product may still contain multi-ring compounds, monofunctional compounds, and high molecular weight tar by-products. The presence of these by-products reduces ultimate molecular weight in polyimides prepared from this monomer. Distillation processes provide levels of purity this high; however, since the monomer is a solid, distillation processes on a manufacturing scale frequently encounter the problem of the monomer crystallizing within the distillation apparatus. Clean-up causes loss of time and loss of yield. Thus, it would be an advantage to be able to provide APB in a process on a manufacturing scale in high yield and at a level of purity that exceeds 99% in order to produce high molecular weight polyimides.

SUMMARY OF THE INVENTION

This invention is a process for purifying 1,3-bis (aminophenoxy benzene) APB) on a manufacturing scale to at least 99.5% purity.

The process comprises the sequential steps of (a) forming the dihydrochloride salt of APB (hereinafter APB-HCl), (b) recrystallizing the APB-HCl from isopropyl alcohol, (c) converting the APB-HCl to free APB.

DETAILED DESCRIPTION OF THE INVENTION

The synthetic route for APB produces a crude APB that is usually 80–90% solids, with the remainder being the organic solvent in which the reactions were conducted. Typically, the solvent is xylene. In manufacturing scale processes, it can be difficult to obtain both purity and high yield. In the inventive recrystallization process for manufacturing scale purification of APB, both high purity and good yield are accomplished.

Step (a). The first step in purifying crude APB is the formation of the hydrochloride salt of APB. For the crude APB used in the experimentation for this invention, the assay was in the range of 90–95% by HPLC (high pressure liquid chromatography). A suitable method entails the following: Crude APB is added to a 15–16% aqueous hydrochloric acid solution that is in a stoichiometric excess of at least 30% relative to the APB. The mixture is heated to about 75° C. to dissolve all the solids and the solution cooled to about 50° C. At this temperature the solution is seeded with APB-HCl and then further cooled to about 10° C. or until the APB-HCl crystallizes from solution. If less than a 30% stoichiometric excess of HCl is used, the APB-HCl salt may form a paste-like agglomeration and be difficult to process.

The crystals are collected by any means known in the art for retrieving crystals from a liquid, such as, for example, vacuum filtering or centrifuging. If vacuum filtering or centrifuging is used, the operation is continued until no additional liquid is recovered. The crystals are rinsed, one time is usually sufficient, with isopropyl alcohol. A typical and sufficient rinse amount is 20% by weight of the crystals, although the amount is not critical and any amount at about 20% will be adequate.

Step (b). The APB-HCl crystals are then recrystallized from isopropyl alcohol. Completely dry APB-HCl is insoluble in isopropyl alcohol; therefore, the crystalline product must contain sufficient water to effect the recrystallization. Water remaining from the aqueous HCl solution will be present with the crystals, unless the crystals were brought to complete dryness when collected in step (a). In the practice of this invention, it has been found that about 10–15% by weight of water remaining with the crystals will permit the crystals to dissolve into the isopropyl alcohol used for the recrystallization. Alternatively, that amount of water can be added to the isopropyl alcohol.

The crystals are added to the isopropyl alcohol in a 1:1.2–1.6 weight ratio (APB-HCl to isopropyl alcohol) and heated to a temperature in the range of 70°–75° C. until the APB-HCl dissolves. The solution is cooled to about 50° C. and APB-HCl is seeded into the solution. The solution is cooled from 50° C. to about 10° C. over a four to five hour period, independent of batch size, to crystallize the APB-HCl. The crystals are recovered from the solution and rinsed with isopropyl alcohol, one time being sufficient. A typical and sufficient rinse amount is 20% by weight of the crystals, although the amount is not critical and any amount in the range will be adequate. At this stage in the process, the yield is about 65–70%.

If a higher yield is desired, the rinse IPA is included with the mother liquor filtrate, and treated with ethyl acetate to crystallize additional APB-HCl. The isopropyl alcohol mother liquor with rinses is heated to a temperature within the range of 70° to 75° C. Ethyl acetate is added in a weight ratio of 1–1.25:1 ethyl acetate to IPA, and at a rate to maintain the temperature of the solution in the range of 65° to 75° C. After the addition of ethyl acetate, the solution is cooled to about 50° C., and then is seeded with ABP-HCl crystals. The solution is cooled to about 10° C. to crystallize additional APB-HCl. The crystals are collected and rinsed with isopropyl alcohol as in the rinsing operation in step (a) after formation of the APB-HCl crystals. The crystals are allowed to retain some water as previously described, and are combined with the crystals previously obtained. This additional step gives ultimate increased yields of 70–75%.

Step (c). In this step, the APB-HCl crystals are converted to the free APB. The APB-HCl crystals are dissolved in water at about 40° C. A sufficient volume of water will be about two times the volume of IPA from which the crystals were precipitated in step (b). The crystals remain in solution even after the solution cools to room temperature.

Optionally, at this point, the APB-HCl solution can be treated with a decolorizing charcoal, in a weight ratio of 1–2:100, charcoal to APB-HCl. The charcoal is added to the solution at room temperature and stirred for about two hours. The charcoal is removed by filtration.

The solution of dissolved APB-HCl, whether by decolorized charcoal or not, is treated as follows: The solution of APB-HCl crystals is added into a solution of 7.5 weight % sodium hydroxide in water (aqueous caustic) and isopropyl alcohol, the solution being in a weight ratio of 3.5–4:1 aqueous caustic to IPA. At this weight ratio, the mixture does not phase separate. The addition into the aqueous caustic and isopropyl alcohol is done slowly, over a period of about 4 to 6 hours, independent of batch size. The presence of the isopropyl alcohol causes the free APB to precipitate as a fine white powder. In the absence of the isopropyl alcohol, the free APB precipitates as a lumpy sludge or oil.

The purified free APB is collected and suspended in cold water to dissolve out any salts. The amount of water is not critical and it has been found that about two times the amount of IPA used to recrystallize the APB-HCl crystals in step (b) is sufficient. The crystals are collected, resuspended in a similar volume of warm water, and then collected.

The product is dried at 70°–80° C. and assays by HPLC at greater than 99.5% purity, in yields of 70–75% percent based on crude starting APB.

A series of synthetic reactions to make polyimides starting with the monomer APB at various levels of purity and a dianhydride were conducted and the resulting molecular weight as shown by inherent viscosity recorded as follows:

| Reaction ID | APB Assay Purity | Inherent Viscosity* Target >0.45 |
|---|---|---|
| A | 99.5 | 0.50 |
| B | 98.8 | 0.32 |
| C | 99.5 | 0.49 |
| D | 98.8 | 0.43 |

Inherent Viscosity correlates to molecular weight and is measured as:

Inherent Viscosity=In(RV)/conc., where In(RV) is the natural log of the relative viscosity, the relative viscosity is the ratio of the viscosity of the solution to the viscosity of the solvent, and conc. is the concentration of the polyimide in grams per dl of solvent.

The target for the synthesized polyimide was greater than 0.45. As seen from the above data, only when the assay purity was at least 99.5% was the molecular weight sufficiently high to meet the target molecular weight.

What is claimed is:

1. A process for obtaining 1,3-bis(aminophenoxy benzene) at a purity of at least 99.5% and a yield of at least 70% on a manufacturing scale comprising (a) converting 1,3-bis(aminophenoxy benzene) to its hydrochloride salt, (b) recrystallizing the hydrochloride salt of 1,3-bis (aminophenoxy benzene) from isopropyl alcohol, (c) reconverting the hydrochloride salt to the purified free 1,3-bis(aminophenoxy benzene), and (d) recovering additional yield from the isopropyl alcohol in step (b) by (i) adding ethyl acetate to the isopropyl alcohol in a weight ratio of 1–1.25:1 ethyl acetate to IPA, (ii) at a temperature of about 50° C. seeding the solution with ABP-HCl crystals, (iii) cooling the solution to about 10° C. to precipitate out additional APB-HCl crystals, and (iv) collecting the APB-HCl crystals.

* * * * *